United States Patent [19]

Blau

[11] Patent Number: 5,372,126

[45] Date of Patent: Dec. 13, 1994

[54] PULMONARY SAMPLING CHAMBER

[76] Inventor: Anthony D. Blau, 314 W. 14th St., New York, N.Y. 10014

[21] Appl. No.: 944,350

[22] Filed: Sep. 14, 1992

[51] Int. Cl.⁵ ............................................. A61M 11/00
[52] U.S. Cl. ............................. 128/200.14; 128/205.12; 128/205.26
[58] Field of Search .................... 128/200.14, 203.12, 128/205.12, 205.29, 909, 760, 716, 205.26

[56] References Cited

U.S. PATENT DOCUMENTS

| | | | |
|---|---|---|---|
| 310,568 | 1/1885 | Emery | 4/535 |
| 360,773 | 4/1887 | Hosford | 604/20 |
| 426,094 | 4/1890 | Tucker | 604/23 |
| 859,156 | 7/1907 | Warnken | 128/205.26 |
| 3,565,072 | 2/1971 | Gauthier | 128/200.16 |
| 3,665,917 | 5/1972 | Jensen | 128/716 |
| 3,703,173 | 11/1972 | Dixon | 128/205.26 |
| 3,745,991 | 7/1973 | Gauthier et al. | 128/205.29 |
| 3,902,488 | 9/1975 | Sheppard | 128/205.26 |
| 4,224,936 | 9/1980 | Cox | 128/205.26 |
| 4,240,444 | 12/1980 | Virgulto et al. | 128/782 |
| 4,454,887 | 6/1984 | Krüger | 128/772 |
| 4,510,929 | 4/1985 | Bordoni | 128/200.14 |
| 4,741,331 | 5/1988 | Wunderlich | 128/200.15 |
| 4,821,715 | 4/1989 | Downing | 128/207.18 |
| 4,881,542 | 11/1989 | Schmidt et al. | 128/207.14 |
| 4,981,466 | 1/1991 | Lumbert | 604/19 |
| 5,233,975 | 8/1993 | Choate | 128/200.14 |

*Primary Examiner*—Edgar S. Burr
*Assistant Examiner*—Aaron J. Lewis
*Attorney, Agent, or Firm*—Robert L. Slater, Jr.

[57] ABSTRACT

A pulmonary sample collection apparatus and method are provided for the sanitary collection of pulmonary sputum samples otherwise referred to as sputum induction, without allowing escape of infectious pathogenic microbes into the ambient air. The present invention is conveniently and safely usable in outpatient settings, such as doctors' offices and laboratories. The apparatus entirely encloses the patient in a chamber. The chamber is equipped with an air exchange blower which produces within the closed chamber controlled negative air pressure. The chamber is equipped with a replacable exhaust filter unit with which to trap airborne pathogens and other potentially harmful particles. The negative internal air pressure acts to facilitate sealing the chamber to prevent escape of substantially all airborne infectious particles from the chamber. The chamber is further provided with a novel hollow three terminal tube arrangement, one arm of which connects through an aperture in the chamber wall to an external aerosol source. The externally positioned aerosol source supplies a copious stream of cough inducing aerosol. A second cross arm of the novel three terminal tube, positioned within the chamber, is terminated in a disposable patient mouthpiece through which the patient inhales and exhales, and the remaining terminal of the three terminal tube is openly vented into the chamber. The patient situated within the negative air pressure of the sealed chamber breaths in a normal manner inhaling externally nebulized aerosol mist introduced through one terminal of the three terminal tube arrangement while coughing and exhaling only into the interior of the sealed chamber. The contaminated air within the chamber is cleared of pathogens and exhausted through disposable filters, the air within the chamber being changed rapidly many times per minute.

8 Claims, 3 Drawing Sheets

PULMONARY SAMPLING CHAMBER

BACKGROUND OF THE INVENTION

Sputum induction [SI] is a technique for obtaining a deep sample of secretions from the lungs in a non-invasive manner for diagnostic purposes from patients who are unable to spontaneously expectorate such material on demand.

The sputum can be examined in a variety of ways, according to the judgment of the clinician, for bacteria, fungi, viruses, parasites, or malignant cells. Alternatively, in recent years, patients undergo an invasive procedure known as fiber optic bronchoscopy in which a thin, flexible tube is guided into the patients lungs allowing for suctioning of material. Bronchoscopy is somewhat uncomfortable, costly, occasionally hazardous, time consuming and usually requires a hospital environment to be accomplished safely.

Sputum induction is a long standing procedure traditionally used to obtain material to confirm the diagnoses of pulmonary tuberculosis, a bacterial infection of the lungs. It is also used to follow, in a serial manner, the effectiveness of therapy for this condition.

The technique of sputum induction essentially comprises having the subject breathe a nebulized mist or aerosol of a liquid which acts as a cough inducing agent, for example hypertonic saline solution. The inhaled saline aerosol or mist humidifies and also irritates the subject's airways, thus promoting and facilitating expectoration of a deep sputum sample.

Sputum induction (SI) has historically been confined to the hospital environment and, more specifically, to institutions with special units for tuberculosis patients. Ordinarily a special space is designated exclusively for sputum induction, since deep coughing can result in the aerosolization of potentially infectious droplet nuclei containing tubercle bacilli, which can be carried by air currents to other areas of a hospital. The prior practice in hospitals has utilized a small room, usually isolated by closing off the outflow ducting of the central air system. In addition, a large exhaust fan is placed in a window of the isolated room to provide for 20 to 30 total room air exchanges per hour. The isolated room has to be located so that contaminated exhaust air will not be pulled into adjacent rooms or building from outside. Ultraviolet light fixtures are placed in the SI room in a manner to sterilize the air and kill aerosolized microorganisms. Even with these precautions, however, it has been estimated that the number of viable organisms released into the air has been reduced by only about 50%. An additional problem has been that of maintaining a comfortable room temperature, since inflowing heated or cooled air is rapidly vented outside.

Sputum induction has, therefore, never gained acceptance as an office procedure due to the cost and inconvenience of dedicating and modifying a separated and isolated space just for SI, and also due to the small but finite hazard of transmission of tuberculosis or other airborne infectious diseases to susceptible persons in the area.

Therapeutic patient enclosures have been known for at least one hundred years. Such patient enclosures are frequently used, for example, to treat patients who must inhale aerosolized medication. Aerosol pentamidine treatment has been administered in this fashion to HIV infected patients to prevent or delay the occurrence of Pneumocystis pneumonia.

Inhaling medication of whatever composition, often induces coughing. Active pulmonary tuberculosis occurs frequently in immunosuppression HIV+ patients. Thus control of sputum droplets exhaled or resulting from coughing in HIV infected patients is well advised to prevent possible spreading of tuberculosis infection. Pentamidine treatment is regularly given to patients in an outpatient setting such as a clinic or doctor's office, to accommodate out patient treatment of HIV patients. Commercial patient enclosures offering protection from contamination of ambient office or clinic air space with tubercle bacilli have been developed. Such enclosures provide for rapid and therefore multiple air exchanges between the patient enclosure interior and the ambient air in the medical office. This rapid exchange is achieved by means of a high volume blower. Infectious particles are trapped within highly efficient air filters. (For instance, a 0.3 micron filter is adequate to entrap most airborne pathogens.)

A problem with patient enclosures which have been used to administer inhaled pentamidine and other drugs is that they are not adapted for sputum induction. SI requires the delivery of a large volume of nebulized mist of externally generated aerosol particles. For instance, an aerosol of hypertonic saline solution has been successfully used for the purpose. Existing commercial enclosures provide some type of small-aperture nozzle mounted to the wall of the chamber. Through such a nozzle a quantity of air with aerosol mist must be generated and delivered to inside the chamber and then to an enclosed patient. The aerosol is thus diffused throughout the chamber, the concentration of the aerosol reaching the patient is relatively low. By providing a frequent change of air within the chamber the aerosol mist is further diluted preventing the patient from receiving a sufficient amount. Alternatively, aerosolized medication may be administered with a small hand held nebulizer held by the patient within the chamber. Available hand held nebulizers are sufficient to aerosolize only small quantities of medication in liquid droplet form. Thus, with either of these methods of supplying the aerosol mist the patient fails to receive a sufficient quantity for SI.

Sputum induction requires that the aerosol mist be provided in a copious and continuous supply to the patient. Accordingly, the patient's air supply must be heavily laden with nebulized aerosol. To be effective for sputum induction the necessary quantity of aerosol is most conveniently generated exterior to the chamber and delivered into the chamber and ultimately directly to the patient through a mouth piece. A significantly large ventilator tubing specially connected for the purpose is required for delivering directly to the patient an adequate copious volume of externally generated aerosal mist for an effective sputum induction procedure.

The central purpose of my invention is to provide means whereby a patient may inhale an air and aerosol agent mixture generated externally of an airtight secure chamber having a controlled negative pressure therein with respect to the ambient atmospheric pressure. In addition, the chamber must be constructed so that substantially all potentially pathogenic airborne particles exhaled or expectorated by the patient while seated within the chamber are entrapped in a disposable air filter mounted at an exhaust port of the closed chamber.

Earlier therapeutic patient enclosures include those such as U.S. Pat. No. 360,733 issued to Hosford. Hosford's device provided a vapor bath for a human patient; however, it did not enclose the patient's head and thus did not control exhaled, airborne infectious particles.

U.S. Pat. No. 3,902,488 issued to Sheppard related to inducing patient hypothermia. Sheppard, too, failed to control escape of infectious airborne particles in his teaching.

U.S. Pat. No. 4,881,542 issued to Schmidt, et al. is directed toward a tubular flexible tracheal sampling probe, and as such teaches invasive pulmonary sampling.

U.S. Pat. No. 4,981,466 to Lumbert is directed to a medical ventilating and venting apparatus and methods in which a catheter tube is used to evacuate lung secretions. Lumbert teaches an invasive medical procedure for obtaining deep lung secretion samples. The present invention, on the other hand, is directed to an entirely noninvasive technique for diagnostic deep pulmonary sampling.

U.S. Pat. No. 426,609 issued to Tucken is directed to a hand-held device to deliver an irritant through a patient mouthpiece. However, there is no provision in the Tucken patent for trapping exhaled infectious particles.

U.S. Pat. No. 310,568 issued to Emery, is directed to a medical vapor generator, but discloses no means for entrapping infectious particles exhaled by a patient.

Viewing together the aforementioned U.S. Patents, none describes an invention such as the present one, which provides for a novel combination of elements for safely inducing sputum induction in potentially or actively infectious patients. With respect to currently commercially available patient enclosures none are known which provide the combination of necessary conditions and structures for conducting safe sputum induction procedures.

OBJECTS OF THE INVENTION

It is an object of the present invention to provide an apparatus for sputum induction pulmonary sampling which is safe, mobile, convenient, compact, sanitary in operation and thus economically and professionally attractive to clinical practitioners in outpatient health facilities.

It is a further object of the present invention to provide a sputum induction apparatus within an enclosure adapted to securely entrap substantially all airborne pathogenic particles. The present invention provides a novel three terminal tubing connection permitting introduction of an aerosol generated externally to the enclosure leading to the patient's airways through a disposable mouthpiece, while permitting the patient to breath normally and confining all patient exhalations and air borne droplets from the patient's coughing to the interior of the chamber where any pathogenic particles may be safely filtered from the air within the chamber before it is returned to the environment in the medical office.

SUMMARY OF THE INVENTION

The present invention provides for a sputum induction apparatus for safely and noninvasively collecting deep pulmonary samples from a patient without risk of spreading infectious microbes into the ambient air surrounding the apparatus. The present invention combines the features of a conventionally ventilated chamber resembling a telephone booth in size and shape, the chamber being equipped with air inflow and forced air exhaust means to maintain a negative atmospheric pressure when in use. An externally positioned compressor-driven nebulizer is connected to the interior of the chamber through flexible ventilator tubing which delivers aerosol mist from the nebulizer through a novel multiple terminal tubing arrangement directly to a patient enclosed within the chamber.

In important part of the novelty of the present invention resides in the three terminal tubing arrangement which provides for a large release of aerosol mist to be delivered to the patient through means which enables the patient to breathe normally while inhaling aerosol mist generated externally of the chamber, and exhaling only into the air confined within the chamber. With this apparatus substantially all of the patients exhaled and cough induced pathogens are filtered out of the air before it is exhausted from the interior of the chamber.

DETAILED DESCRIPTION OF THE INVENTION

Figure 1:
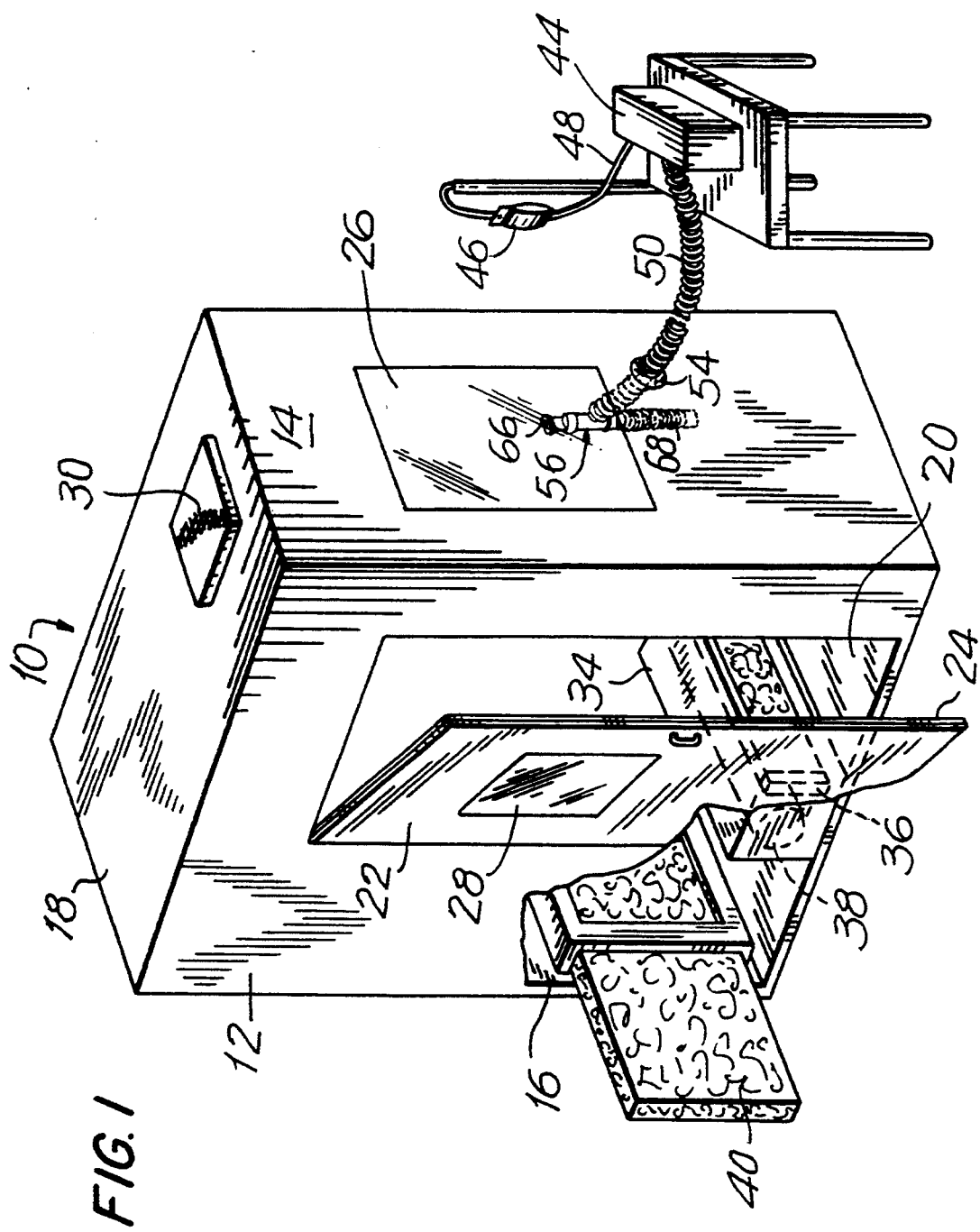
FIG. 1 is a perspective view, partly cutaway, illustrating a preferred embodiment of my invention.
Figure 2:
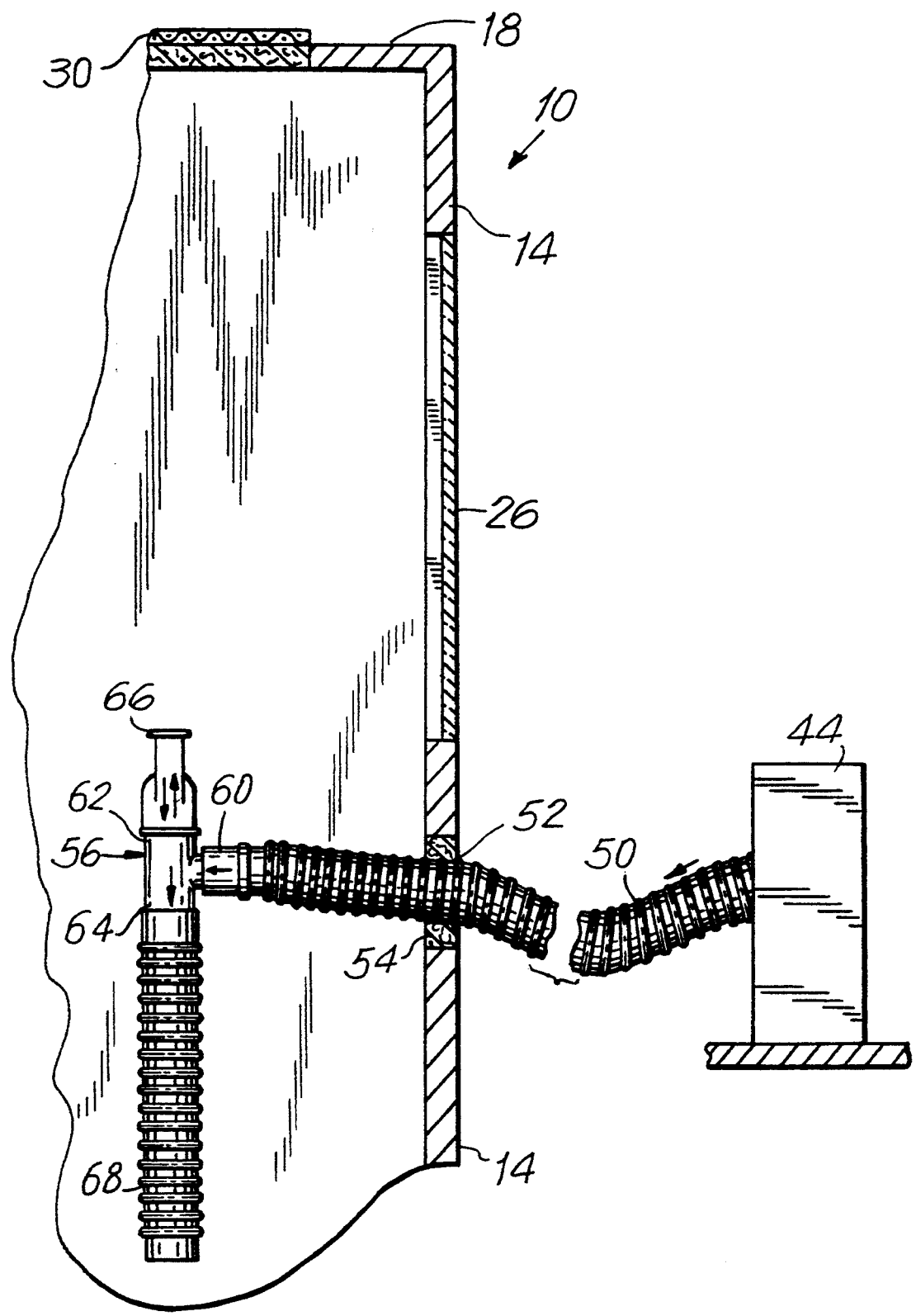
FIG. 2 is a detailed view of tubing arrangement in the embodiment of my invention shown in FIG. 1 for introducing a mixture of air and aerosol mist to a patient within an enclosure while confining the patients exhalations to the interior of the enclosure.
Figure 3:
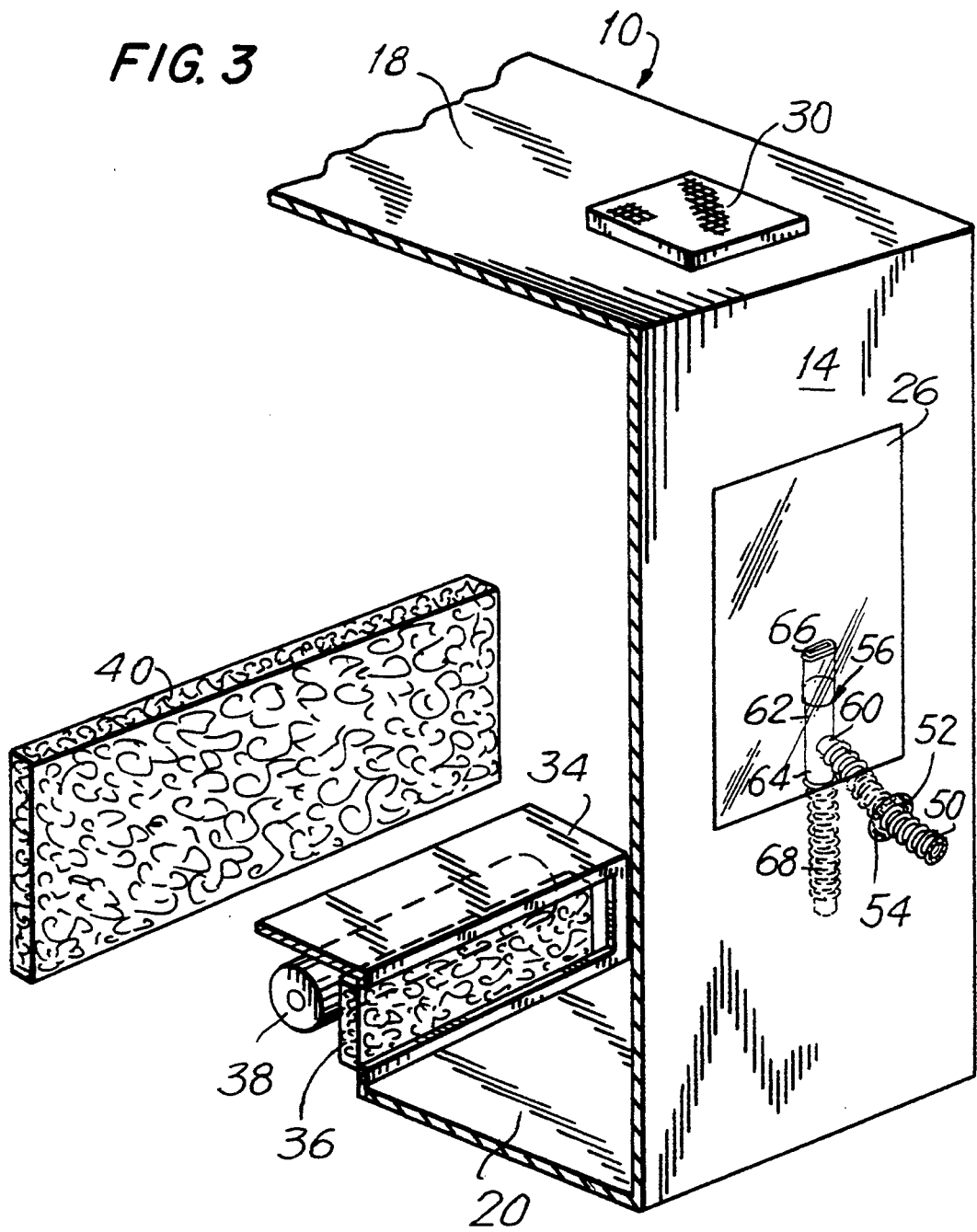
FIG. 3 is a schematic view of the component parts of the embodiment of my invention illustrated in FIG. 1 which further illustrates the control means for regulating a negative pressure within an enclosure, the flow of incoming air, the aerosol mist, the patients exhalation of cough induced particles, and the filtered air exhausted into the ambient atmosphere external of the enclosure.

Referring to the illustrations, FIG. 1 is a partly cutaway perspective view of my invention. An enclosed airtight chamber 10 comprised of a rear panel, front panel 12; side panels 14, 16, top panel 18 and floor 20. A door 22 is mounted in the front panel 12 to permit a patient entrance into and from the interior of the chamber 10. The door 22 is equipped with an airtight sealing gasket 24 about its perimeter. A sealed window 26 is mounted in the side panel 14. Other transparent windows, such as window 28 mounted in door 22, are provided for the comfort and observation of a patient seated in the closed chamber.

The top panel 18 is fitted with an intake air filter 30 positioned within an aperture within the top panel 18. The intake air filter 30 provides significant air flow resistance to the incoming air. Accordingly, a negative air pressure less than ambient atmospheric pressure may be maintained within the chamber when a forced exhaust air flow is maintained. Description of the exhaust air flow blower means and filter means is provided below.

Interior of the chamber 10, a seat 34 is situated upon which a patient may be comfortably seated. It is convenient to position the air exhaust filters and exhaust blower beneath and behind the seat 34. A readily replaceable exhaust air prefilter 36 is shown mounted below the seat 34. An electric powered high volume blower air pump 38 is mounted down stream adjacent to the exhaust prefilter 36 in the exhaust air stream. The exhaust blower provides a flow rate of between 150 and 270 cubic feet of air per minute. The exhaust air blower is capable of completely exchanging the air within the chamber between 250 and 460 times per hour. Thus a continuous supply of fresh air at a negative pressure is provided within the chamber. The exhaust air is cleared by the filters of pathogens and returned to the exterior of the chamber without temperature change.

A readily replaceable main exhaust filter 40 is shown mounted in the side panel 16, airtight ducting confines the exhaust air stream from the prefilter 36 through blower 38 and into the main filter 40.

The exhaust prefilter 36 and the main filter 40 entrap all particulate matter larger than 0.3 microns. Commercial disposable filters of such fine porosity are readily available and assure substantially total removal of pathogens from the exhaust airstream.

The negative air pressure within the chamber is achieved with selecting the filters 30, 36 and 40 with respect to size, resistance to passage of air there through and the relative positioning of the exhaust filters 36 and 40 with respect to the blower 38.

The intake air filter 30 is substantially smaller in area and has substantially greater resistance to passage of air there through than either, respectively, that of the prefilter 36 or the exhaust filter 40. The prefilter 36 has an area smaller than that of the exhaust filter 40. Moreover the resistance of air passage through the prefilter 36 is greater than that through the exhaust filter 40. The prefilter 36 is mounted at the intake port of the high volume blower 38. The high volume blower 38 draws air through the prefilter 36 in part due to reduced pressure resulting from the action of the high volume exhaust blower 38 intake air stream. Thus, a region of slightly lower air pressure than that inside the chamber proper is maintained in the exhaust ducting in the space between the exhaust side of the prefilter 36 and the intake port of blower 38. Thus, flow of air in the exhaust direction is maintained through the prefilter 36.

In order to maintain the required volume exhaust flow through the exhaust filter 40, the ducted space between the output port of the blower 38 and the inner surface of the exhaust filter 40 is maintained at a positive or greater than atmospheric pressure, thus providing the pressure differential to sustain volume flow of air through the filter 40 into the ambient atmosphere.

A negative differential of between 4 and 20 millibars of air pressure with respect to ambiant atmosphere air pressure may be readily maintained within the sealed chamber when the high volume blower is in operation and the filters having the resistance, respectively, as described above are mounted in place.

A conventional compressor driven aerosol nebulizer 44 is positioned exteriorly to the chamber 10. Aerosol nebulizers are commercially available; a Ultra Neb 99 device manufactured by the DeVilbiss Company of Medford, Pa. has been used successfully in my sputum induction system. The aerosol mist is generated by gravity feeding hypertonic saline or other appropriate liquid solution from a reservoir 46 connected through plastic tubing 48 to the inlet orifice of the aerosol nebulizer 44. A hypertonic saline solution in the reservoir 46 when mixed with a rapidly moving air stream within the nebulizer produces an aerosolized air mixture well adapted to sputum induction.

The output port (not shown in the illustrations) of the aerosol nebulizer 44, feeds a mixture of aerosol and air generated within the nebulizer into a flexible ventilator tube 50. The tube of approximately one inch diameter provides sufficient flow and therefore volume of aerosol and air mixture. The ventilator tube 50 is passed through an aperture 52 located in the chamber side panel 14. Packing material 54 may be placed around the ventilator tube 50 at the aperture 52 to prevent leakage.

The ventilator tube 50 terminates within the chamber. A hollow three terminal or T-shaped tube 56 having a base arm 60 and cross arms 62 and 64 is connected through the base arm 60 to the terminal of the ventilator tube 50. By this arrangement a voluminous continuous supply of aerosol and air mixture flows to the patient through cross arm 62. While some portion of the aerosol mist is introduced into the interior of the chamber through the cross arm 64, the patients inhalations through cross arm 62 absorbs the largest portion of the aerosol flowing through the ventilator tube 50. This favorable proportional utilization of the aerosol mist is readily achieved by adjusting the rate of flow of aerosol from the nebulizer 44.

The ventilator tube 50 carries aerosol mist at a slight positive pressure above ambient atmospheric pressure from the nebulizer 44 into the interior of the chamber 10. The chamber 10 when in use is maintained at a negative pressure with respect the ambient atmospheric pressure. The air and aerosol mixture entering the chamber through the ventilator tube 50 add only a small portion of the volume of air flowing into the chamber.

When the patient is seated within the closed and sealed chamber and the air pressure within the chamber is slightly reduced by means as described above, the sputum induction procedure may be commenced. The patient then places the mouth piece 66 within his mouth. Nebulized aerosol is then fed through the ventilator tube 50 into the base arm 60 of the three terminal tubing. The patient then breathes through the cross arm 62, both inhaling and exhaling. Exhalation from the patient, however, passes through the cross arm section 64 and the exhalation tube 68 and into the interior of chamber 10. Exhalation by the patient back into the ventilator tube 50, is prevented by the pressure gradient created by the positive air pressure within the ventilator tube 50. Due to the reduced or negative pressure within the interior of the chamber 10, therefore within the three terminal tubing 56, the aerosol flows into the tubing 56 through cross arm 62 and directly to the patient. Particulate matter exhaled by the patient or spray of sputum droplets resulting from coughing by the patient are securely contained within the chamber and safely collected in the disposable exhaust filters 36 and 40.

The forgoing description is of a preferred embodiment of my invention. Other means to facilitate the different functions of my novel apparatus may be suggested and the whole apparatus still will be within the intended scope of my invention. For instance, the negative pressure within the closed chamber of my invention could readily be maintained with means different than that described in the aforesaid preferred embodiment without altering the scope or intented function of my invention. The full scope of my invention is more fully defined in the claims set forth below.

I claim:

1. An apparatus for safely conducting non-invasive sputum induction procedures comprising a hollow three terminal tubing means, a source of aerosol for inducing a patient to cough, a sealable inclosure adequate to fully enclose a patient, air intake and air exhaust means for changing the air within the enclosure, replaceable filter means mounted to the air exhaust means of the enclosure, said filter means adapted to clean exhaust air from the enclosure of substantially all particulate matter and pathogens, the source of aerosol being connected to one terminal of the hollow three terminal means, a second terminal of the three terminal means being vented into the enclosure and the third terminal of the three terminal means adapted for the patient to breath through normally, whereby while administering aerosol mist to a patient, the patient's exhalations and sputum droplets from coughing are isolated from the inflowing aerosol and from the ambient air exterior of the enclosure.

2. An apparatus for safely conducting noninvasive sputum induction procedures wherein patient exhalation pathogens and sputum droplets from coughing are controlled for safe disposal comprising a hollow three terminal tubing means; means for generating a copious quality of aerosol; means for fully enclosing a patient, said means for enclosing a patient being provided with means for making numerous changes of air each minute within the enclosure while maintaining a negative pressure within the enclosure with respect to the ambient atmosphere, replaceable filter means; the filter means mounted on the enclosure to provide cleansing of the exhaust air stream as it is removed from the enclosure, where with the hollow three terminal tubing means is positioned within the enclosure, the first terminal thereof being connected to the aerosol generating means, the third terminal thereof venting into the enclosure and the second terminal thereof being available through which a patient may inhale and exhale, whereby the patient breathing through the second terminal may inhale and exhale normally, inhaling aerosol supplied through the first terminal of the hollow three terminal tubing, while the patient's exhalations pass through the hollow three terminal tubing and are vented into the enclosure through the third terminal.

3. Apparatus for safely conducting non-invasive sputum induction procedures comprising a sealable chamber in which a patient may be enclosed, means for exchanging the entire air content within the chamber a number of times per minute while steadily maintaining the air pressure within the chamber below the ambient air pressure, filter means for cleansing the air removed from the interior of the chamber prior to its exhaust into the ambient atmosphere, means for generating a copious stream of aerosol mist exterior of the chamber, ventilator tubing connecting the aerosol generating means to the interior of the chamber for conducting the stream of aerosol mist into the interior of the chamber, a hollow three terminal means, the ventilator tubing being connected within the chamber to one terminal of the three terminal tubing means, a patient mouthpiece, the mouthpiece being attached to a second terminal of the hollow three terminal tubing means and the third terminal of the three terminal tubing means being vented within the interior of the chamber, whereby a patient positioned within the sealed chamber may while breathing normally through the mouthpiece inhale copious quantities of aerosol, while the patient's exhalations and cough induced droplets are securely retained within the chamber and are filtered out of the interior chamber air prior to returning the chamber air to the atmosphere exterior of the chamber.

4. The apparatus of claim 3 in which the aerosol mist is generated by passing a rapidly moving stream of air over the surfaces of a quantity of an hypertonic saline solution.

5. The apparatus of claim 3 in which a negative pressure is maintained within the chamber by means of an intake air filter, replaceable exhaust air filters, and a high volume air blower, the resistance to passage of air through the intake air filter being greater than the resistance of the passage of air through the exhaust filters, the air blower being positioned adjacent to the exhaust air filters whereby the blower forces a larger quantity of air through the exhaust filters than passes through the higher resistance air intake filter resulting in a reduced air pressure within the chamber.

6. The apparatus as in claim 3 in which the hollow three terminal tube means is a hollow T tube.

7. The apparatus of claim 3 wherein the negative air pressure within the interior of the chamber provides an inflow of air and is an effective seal preventing airborne particles from exiting the chamber at the site of any structural disintegrity of the chamber.

8. A noninvasive safe and sanitary method of deep pulmonary sputum sampling comprising the steps of:
   a. placing the patient within a ventilated sealed chamber;
   b. producing a small negative air pressure within the chamber;
   c. directing a stream of exhaust air from the interior of the chamber through a filter;
   d. delivering to a patient within the chamber through a disposable mouthpiece an aerosol mist, wherein the mouthpiece is connected to a disposable hollow three terminal tube means for receiving externally generated aerosol;
   e. allowing the patient enclosed within the chamber to inhale the aerosol mist through the mouthpiece while exhaling normally and without removing the mouthpiece to induce coughing, and in turn aid the patient to produce and collect a deep pulmonary sputum sample.

* * * * *